United States Patent
Kopperschmidt et al.

(10) Patent No.: US 11,298,450 B2
(45) Date of Patent: Apr. 12, 2022

(54) APPARATUS FOR THE NON-INVASIVE MEASUREMENT OF THE BLOOD FLOW

(71) Applicant: FRESENIUS MEDICAL CARE DEUTSCHLAND GMBH, Bad Homburg (DE)

(72) Inventors: Pascal Kopperschmidt, Dittelbrunn (DE); Carsten Mueller, Euerbach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 645 days.

(21) Appl. No.: 15/316,604

(22) PCT Filed: Jun. 1, 2015

(86) PCT No.: PCT/EP2015/001107
§ 371 (c)(1),
(2) Date: Dec. 6, 2016

(87) PCT Pub. No.: WO2015/185202
PCT Pub. Date: Dec. 10, 2015

(65) Prior Publication Data
US 2018/0185565 A1    Jul. 5, 2018

(30) Foreign Application Priority Data
Jun. 6, 2014   (DE) .................... 10 2014 008 446.9

(51) Int. Cl.
*A61M 1/36* (2006.01)
*A61B 5/026* (2006.01)
(Continued)

(52) U.S. Cl.
CPC ......... *A61M 1/3656* (2014.02); *A61B 5/0036* (2018.08); *A61B 5/026* (2013.01);
(Continued)

(58) Field of Classification Search
CPC .............. A61M 1/3656; A61M 1/3655; A61M 2205/3331; A61M 2205/3368; A61M 2205/3334; A61B 5/0261
See application file for complete search history.

(56) References Cited

U.S. PATENT DOCUMENTS 4,548,516 A * 10/1985 Helenowski ........... A61B 5/028
374/135
5,690,115 A   11/1997 Feidman et al.
(Continued)

FOREIGN PATENT DOCUMENTS

DE   202012005321        10/2013
GB        2377489 A  *  1/2003  ......... A61B 5/14552
(Continued)

*Primary Examiner* — Rene T Towa
(74) *Attorney, Agent, or Firm* — Jacobson Holman PLLC

(57) ABSTRACT

An apparatus for the non-invasive measurement of the blood flow through a shunt of a patient has at least one bandage which can be worn by the patient, as well as a plurality of sensors which are arranged in or at the bandage, which are arranged in at least one multidimensional matrix, and which are configured such that they create a multidimensional matrix of measured values of at least one parameter detected by the sensors.

11 Claims, 2 Drawing Sheets

(51) Int. Cl.
*A61B 5/00* (2006.01)
*A61B 5/1455* (2006.01)
*A61B 5/01* (2006.01)
*A61B 5/282* (2021.01)
*A61B 5/335* (2021.01)
*A61B 5/352* (2021.01)

(52) U.S. Cl.
CPC ......... *A61B 5/6831* (2013.01); *A61M 1/3655* (2013.01); *A61B 5/015* (2013.01); *A61B 5/0261* (2013.01); *A61B 5/14552* (2013.01); *A61B 5/282* (2021.01); *A61B 5/335* (2021.01); *A61B 5/352* (2021.01); *A61B 5/6802* (2013.01); *A61B 2562/0261* (2013.01); *A61B 2562/046* (2013.01); *A61B 2562/066* (2013.01); *A61B 2562/164* (2013.01); *A61M 2205/3306* (2013.01); *A61M 2205/3331* (2013.01); *A61M 2205/3334* (2013.01); *A61M 2205/3368* (2013.01); *A61M 2205/3569* (2013.01); *A61M 2205/3673* (2013.01); *A61M 2205/52* (2013.01); *A61M 2205/702* (2013.01); *A61M 2230/04* (2013.01)

(56) References Cited

U.S. PATENT DOCUMENTS

| | | | |
|---|---|---|---|
| 5,724,025 A * | 3/1998 | Tavori | A61B 5/0002 340/573.1 |
| 6,533,729 B1 | 3/2003 | Khair et al. | |
| 6,725,072 B2 | 4/2004 | Steuer et al. | |
| 7,368,855 B2 | 5/2008 | Orten | |
| 2002/0099286 A1 | 7/2002 | Sandler et al. | |
| 2003/0167080 A1 * | 9/2003 | Hart | A61N 5/0616 607/88 |
| 2008/0139953 A1 * | 6/2008 | Baker | A61B 5/0006 600/509 |
| 2009/0048526 A1 * | 2/2009 | Aarts | A61B 5/02438 600/508 |
| 2009/0292195 A1 * | 11/2009 | Boyden | A61B 5/02007 600/407 |
| 2011/0077537 A1 * | 3/2011 | Ebara | A61B 5/0245 600/500 |
| 2011/0208071 A1 * | 8/2011 | Lu | A61B 5/02125 600/500 |
| 2011/0208073 A1 * | 8/2011 | Matsukawa | A61B 5/6822 600/508 |
| 2015/0031964 A1 * | 1/2015 | Bly | G16H 40/67 600/301 |
| 2016/0022157 A1 * | 1/2016 | Melker | A61B 5/02108 600/407 |

FOREIGN PATENT DOCUMENTS

| | | |
|---|---|---|
| JP | 2002315826 | 10/2002 |
| WO | WO 2012/163738 | 12/2012 |

* cited by examiner

200

APPARATUS FOR THE NON-INVASIVE MEASUREMENT OF THE BLOOD FLOW

BACKGROUND OF THE INVENTION

1. Field of the Invention

The present invention relates to an apparatus for the non-invasive measurement of the blood flow through a shunt of a patient.

2. Description of Related Art

In the area of blood purification by hemodialysis, hemofiltration or hemodiafiltration, it is known to use a shunt from which blood is extracted for extracorporeal purification and into which blood is returned after the extracorporeal purification. The shunt has throughflow rates of the blood in the functional state which are sufficient for the carrying out of the extracorporeal blood purification. The function of the shunt is thus indispensable for adequate hemodialysis, etc.

A shunt no longer sufficiently supplied with blood has effects on the course of the treatment during dialysis treatment in that, for example, arterial pressure alarms occur or in that only a low achievable alarm-free blood flow can be achieved and also has effects on the success of the treatment to the effect that the blood purification or the clearance is limited.

A shunt can be provided by a surgical intervention in which a connection is established between an artery and a vein which is called a native fistula. In another shunt type, an intermediate piece can be inserted by means of a surgical intervention which intermediate piece comprises either a tubular, artificial material or a part of a blood vessel of the body and is utilized as a connection between an artery and a vein. This intermediate piece is also called a graft.

Since the shunt is subject to great wear due to the frequent punctures over the years, a change in the vessel wall of the shunt cannot be avoided. Stenoses, intimal hyperplasia or thromboses can thus impair the shunt function or make it completely unusable. This typically makes a stay in a clinic necessary so that an existing shunt can be revised or a new shunt can be implanted.

If a shunt changes its flow behavior, this is frequently only noticed at the start of the next dialysis treatment, for example by repeatedly occurring pressure alarms on the setting of the blood flow parameters usual for the patient or also later in the process due to much lower measured clearance values which can be ascribed to the low throughflow of the shunt and thus to a comparatively small amount of the purified blood. Under certain circumstances, the dialysis treatment cannot be carried out as planned due to a sealed shunt and an alternative access has to be implanted directly or surgically such as a Sheldon catheter, a central nervous catheter, etc.

Functional limitations of the shunt often remain unnoticed by the patient in the phase between the treatments, i.e. in the interdialytic time period.

An optical sensor is known from U.S. Pat. No. 6,725,072 B2 which serves the non-invasive measurement of blood parameters and in particular the measurement of the blood flow in a vessel access. U.S. Pat. No. 5,690,115 describes an apparatus for measuring the blood flow in a shunt by means of a Doppler system. A bandage is known from JP 2002/315826 which has the object of protecting a shunt access due to its damping properties. DE 20 2012 005 321 U1 discloses a diagnostic plaster having a carrier for electronic components. The diagnostic plaster is used, for example, for detecting ECG data.

SUMMARY OF THE INVENTION

It is the underlying object of the present invention to provide an apparatus and a method by means of which statements on the functional state of a shunt can be reliably made.

This object is achieved by an apparatus, and a method, having the features described herein.

The inventive apparatus comprises at least one bandage which can be worn by the patient as well as a plurality of sensors which are arranged in or at the bandage, which are arranged in at least one multidimensional matrix and which are configured such that they create a multidimensional matrix of measured values of at least one parameter detected by the sensors. The sensors can be integrated into the bandage or can be located at the bandage, in particular at its surface.

The term "bandage" is to be understood generally and comprises any cuff, which can preferably be worn on the arm of the patient, or the like which is suitable to receive a plurality of sensors.

Every shunt has a typical movement and expansion pattern due to the pulsating throughflow. This pulsating temporal volume change can be easily detected by means of a preferably two-dimensional sensor matrix, i.e. with a preferably two-dimensional arrangement of sensors in accordance with the invention.

It is conceivable that stretch sensors are used which are arranged in a two-dimensional matrix for creating a spatio-temporal pattern of the spatial, two-dimensional or three-dimensional stretching of the skin surface over the shunt. The vessel expansion directly at the shunt oscillating with the blood flow can be detected via stretch sensors worked into the bandage, for example.

Piezo sensors in a two-dimensional matrix for creating a spatio-temporal pattern of the stretching forces of the skin surface over the shunt are also conceivable and covered by the invention.

Since the pulsating and thus temporally variable volume change is accompanied by temperature changes at the skin surface, temperature sensors can also be used. They can be used in a two-dimensional matrix for creating a spatio-temporal pattern of the temperature at the skin surface over the shunt.

In accordance with the invention, optical sensors, and in particular optical reflection sensors, can also be used which are arranged in a two-dimensional matrix. These sensors measure through the skin tissue layers and detect pulsating flow changes. They serve the preparation of a spatio-temporal pattern of the blood quantity in the region below the skin surface and preferably above the shunt. For example, LEDs or other sources emitting light in the visible range, or also in the IR range, for the measurement of blood absorption serve as the light source. The LEDs can be introduced into the fabric of the bandage, for example.

The bandage fabric is preferably permeable for light or for IR light.

A spatio-temporal pattern is to be understood as a two-dimensional or multi-dimensional pattern which reproduces the measured values of the sensors simultaneously at specific points in time or permanently.

The correct or deficient function of a shunt can be characterized via the spatially resolved amplitude or via the exceeding or falling below of limit values, and changes in the spatial and/or temporal flow behavior of the blood through the shunt can preferably be recognized via the change in the measured values.

Furthermore, motion sensors and/or accelerometers can be provided which contribute to artefact suppression of movements and measured signals due to muscle tightening and thus reduce the probability for the occurrence of incorrect measurements.

One or more sensors which measure the heart activity such as a sensor for detecting the pulse or an ECG sensor can furthermore be provided.

Since the movement and stretch pattern of the shunt or of the skin is in a time correlation with the ECG or with the heart activity, an association of the measured value with the heart activity can be carried out, for example, via the measurement of the heart activity. For example, the R wave can serve as an orientation point for the measured values or for their comparison with reference values.

The sensors can be configured such that they detect at least one property of the skin. Alternatively or additionally, sensors can be used which detect at least one property of a region disposed beneath the skin and in particular beneath the shunt.

It is furthermore conceivable that the apparatus is configured such that the sensors detect an absolute value of the measured parameter such as the respective present skin temperature. The case is, however, also covered by the invention that the sensors output a value which is representative of the deviation of the measured value from one or more limit values. For example, only the value 0 or 1 or −1 and 1 or the colors black or white or other color combinations can be output depending on whether the measured value is below or above a limit value.

The apparatus can have an indicator device such as a display by means of which the values measured by the sensors or values based thereon such as colors are displayed. This indicator device can be configured as multi-dimensional and in particular as two-dimensional and can display the values respectively measured by the sensors next to one another, preferably in a two-dimensional matrix at specific measurement time points.

Provision is made in a further embodiment of the invention that the apparatus has at least one evaluation unit, with the evaluation unit being configured such that it evaluates the values detected by the sensors. This evaluation can lie, for example, in a comparison between the measured values and desired values or the desired value ranges.

Provision can furthermore be made that the apparatus has at least one memory and that reference data for the values measured by means of the sensors are stored in the memory.

In this respect, the evaluation unit can be configured such that it compares the values detected by the sensors with the reference data. The reference data can be present as a two-dimensional pattern or as a multi-dimensional pattern. A signal or a piece of information can then be output to e.g. a dialysis center on the basis of this comparison.

It is conceivable that a typical functional profile. i.e. typical sensor values, is/are stored and that they are then stored in a memory. This functional profile can then be compared with the actual values of the measurements and on the basis thereof a conclusion can be drawn on the functional state of the shunt.

This functional profile can be stored in dependence on one or more parameters such as the movement, the heat rate, the time of day, etc. and can be used as a reference for the following monitoring.

If one or more of the measurement values changes permanently and constantly from the stored reference model, the recognized deviations are read out to the patient fully automatically or on a prompt to the patient and are, for example, transmitted to a dialysis center. The treating physician can initiate further steps such as an examination appointment for an imaging shunt monitoring, etc. in the dialysis center.

Provision is preferably made that the apparatus has a transmission unit which is in communication with the evaluation unit and which is configured such that it transmits the result of the evaluation carried out in the evaluation unit to a receiver, preferably wireless or by another means. A monitoring of the flow properties of the shunt in the dialysis-free time is in this manner conceivable permanently or taking place at specific points in time in a hardly noticeable fashion for the patient.

The transmission unit can report to the patient and/or to a treatment center or to a clinic so that the patient's shunt can already be checked and corrected as necessary before the next treatment in the dialysis center. In this manner, critical situations or an underdialysis on the day of dialysis can be avoided or reduced due to the known situation of the shunt. Apart from this, an adaptation of the dialysis parameters to the functional state of the shunt is conceivable so that a sufficient dialysis treatment can be carried out despite a functional impairment.

Provision is preferably made that the evaluation unit and/or the memory is arranged in or at the bandage. An "intelligent" shunt bandage is thus conceivable which preferably has the function of the protection of the shunt from mechanical influences on dialysis-free days.

The evaluation unit can be formed by one or more microcontrollers which are coupled to the sensors directly or by wire or wirelessly.

The evaluation unit and/or the memory and/or an energy supply can be worked into the bandage or arranged at the bandage—in accordance with the technology of "wearable electronics".

The apparatus can have an energy source, with provision preferably being made that the energy source comprises or consists of Peltier elements. The power supply of the evaluation unit is thus, for example, possible via thermal "energy harvesting" via one or more Peltier elements deployed in the bandage.

The present invention furthermore relates to a method for the non-invasive measurement of the blood flow through a shunt of a patient, wherein the method is carried out by means of the apparatus described herein, and to the step of applying the bandage to the patient and to the detection of measured values of at least one parameter by means of the sensors of the bandage which are arranged in a multi-dimensional matrix.

The method preferably comprises the step of comparing the measured values detected by means of the sensors with at least one reference value, preferably with at least one reference pattern. This reference pattern can be stored as a "functional profile" of the shunt in dependence on one or more parameters such as the movement, the heart rate, the time of day and can then be used as a comparison pattern for the following monitoring processes.

The method is preferably configured in accordance with one of the claims of the apparatus whose features are described in more detail above.

It is furthermore conceivable that the method comprises the step of transmitting the measured values and/or the step of transmitting the result of the comparison between the measured values and the reference pattern or patterns or other reference values.

BRIEF DESCRIPTION OF THE DRAWINGS

Further advantages and particulars of the invention will be explained in more detail with reference to an embodiment shown in the drawing. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
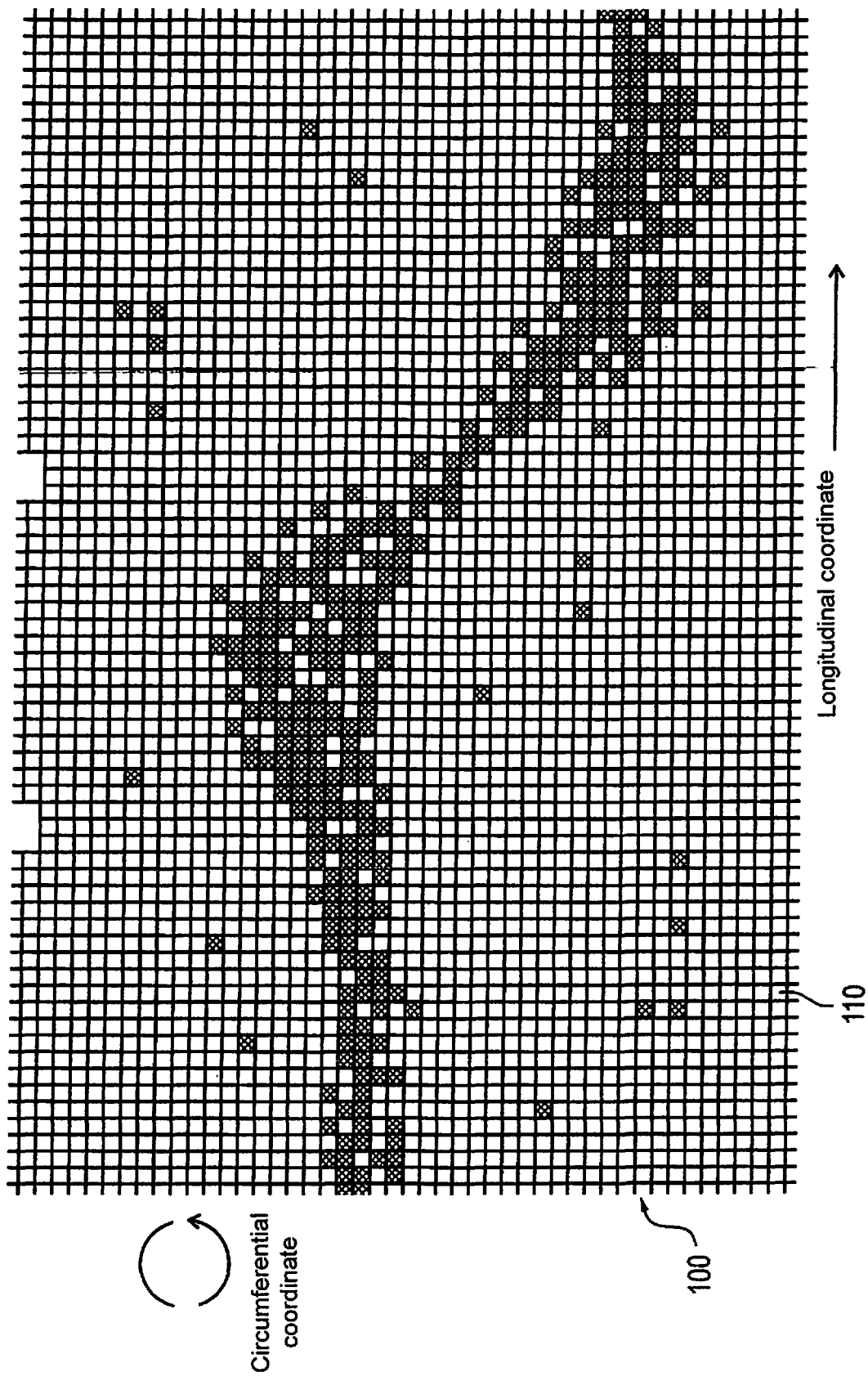
FIG. 1: an exemplary representation of a two-dimensional pattern of the pressures detected by means of the sensors.

The two-dimensional pressure pattern 100 in accordance with FIG. 1 was determined by means of a two-dimensional matrix of sensors whose number and arrangement correspond to those of the individual fields in FIG. 1.

Every individual sensor detects the pressure on the skin of the patient. The pressure pattern comprises white and black boxes 110, with each white box corresponding to a pressure value which lies below a limit value and each black box corresponding to a pressure value which lies above a limit value. The longitudinal coordinate represents the lateral direction of the sensor matrix in the direction of the arm and the ordinate, i.e. the circumferential coordinate, represents the extent along the circumference of the arm around which the bandage is wound.

As can be seen from FIG. 1, two-dimensional patterns 100 of pressure values generated at the same time can be generated in which spatial zones having large pressure values can be differentiated from spatial zones having low pressure values.

A color form of the fields is furthermore conceivable which could provide a conclusion on the level of the pressure per sensor element.

The measurement with optical, thermal or other sensors delivers similar functional patterns of the shunt.

The pattern shown in FIG. 1 can be stored in a memory and can be used as a reference for future measurements. If they differ from the reference pattern, this can be evaluated as an indication of a flow change through the shunt.

The pattern can always be recorded at a specific point in time for purposes of comparability, for example on or directly after the occurrence of the R wave of the ECG.

An evaluation unit can carry out the comparison between the recorded pattern and a reference pattern; the evaluation unit provides the result of the evaluation for recall or transmits it to a receiver, e.g. in a dialysis center. The evaluation can generally take place directly in the bandage or also remote therefrom. In the latter case, it is not the evaluation which is transmitted by means of a transmission unit, but the measured values.

In a preferred embodiment of the invention, the evaluation unit, e.g. in the form of a microcontroller, the memory and the sensors are integrated in or arranged at the bandage.

Figure 2:
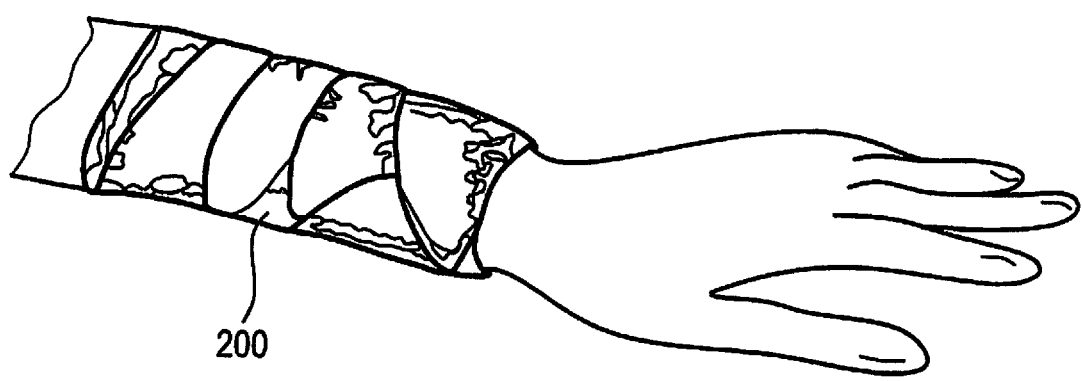
FIG. 2: a perspective representation of the bandage in accordance with the invention.

Such a bandage is shown by the reference numeral 200 in FIG. 2. It can be used for protecting the shunt from external influences in the dialysis-free times. The bandage 200 is thus multi-functional in that, on the one hand, it provides a mechanical protection of the shunt and, on the other hand, carries out a multi-dimensional detection of at least one parameter which allows conclusions on the state of the shunt.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for non-invasive measurement of blood flow through a shunt of a patient, said apparatus comprising:
    a bandage configured to be worn by the patient;
    a plurality of skin stretching sensors arranged at the bandage, the skin stretching sensors being arranged in a multidimensional matrix, and being configured to measure values resulting from a multidimensional pattern of skin stretching that is associated with oscillating variations in blood pressure and ultimately the blood flow through the shunt;
    an evaluation unit configured to process the measured values including generating a spatio-temporal pattern of the spatial stretching of a surface of the skin which reproduces the measured values of the skin stretching sensors simultaneously, and comparing the measured stretching values with reference values so as to generate a pattern providing a comparison of the measured stretching values relative to the reference values, the generated pattern including white and black boxes, with each white box corresponding to a pressure value which lies below a reference value and each black box corresponding to a pressure value which lies above a reference value;
    a transmission unit configured to be in communication with the evaluation unit and to transmit the generated pattern therefrom; and
    a receiver configured to receive the generated pattern transmitted by the transmission unit so as to facilitate treatment of the patient based on the non-invasive measurement.

2. The apparatus in accordance with claim 1, wherein the matrix is a two-dimensional matrix and the pattern is a two-dimensional pattern.

3. The apparatus in accordance with claim 1, further comprising sensors for detecting a heart activity of the patient.

4. The apparatus in accordance with claim 1, wherein the measured values are absolute values.

5. The apparatus in accordance with claim 1, further comprising a memory to store the measured values.

6. The apparatus according to claim 5, Therein the memory is arranged at the bandage.

7. The apparatus according to claim 1, wherein the transmission unit is configured for wireless transmission.

8. The apparatus in accordance with claim 1, wherein the evaluation unit is arranged at the bandage.

9. The apparatus in accordance with claim 1, further comprising a Peltier element as an energy source.

10. A method of non-invasive measurement of blood flow through a shunt of a patient, said method comprising:
providing an apparatus for the non-invasive measurement of the blood flow through the shunt, the apparatus including
a bandage configured to be worn by the patient and having a plurality of skin stretching sensors arranged at the bandage, the skin stretching sensors being arranged in a multidimensional matrix, and being configured to measure values resulting from a multidimensional pattern of skin stretching that is associated with oscillating variations in blood pressure and ultimately the blood flow through the shunt,
An evaluation unit,
a transmission unit in communication with the evaluation unit, and
a receiver,
applying the bandage to the patient;
with the evaluation unit, processing the measured values, including generating a spatio-temporal pattern of the spatial stretching of a surface of the skin which reproduces the measured values of the skin stretching sensors simultaneously, and comparing the measured stretching values with reference values so as to generate a pattern providing a comparison of the measured stretching values relative to the reference values, the generated pattern including white and black boxes, with each white box corresponding to a pressure value which lies below a reference value and each black box corresponding to a pressure value which lies above a reference value;
with the transmission unit, transmitting the generated pattern therefrom; and
with the receiver, receiving the generated pattern transmitted by the transmission unit so as to facilitate treatment of the patient based on the non-invasive measurement.

11. The method according to claim 10, wherein the transmitting is wireless.

* * * * *